(12) United States Patent
Orpana (10) Patent No.: US 8,822,154 B2
(45) Date of Patent: Sep. 2, 2014

(54) METHOD FOR SYNTHESIZING DNA STRAND

(75) Inventor: Arto Orpana, Helsinki (FI)

(73) Assignee: Expression Analytics Oy, Espoo (FI)

(*) Notice: Subject to any disclaimer, the term of this patent is extended or adjusted under 35 U.S.C. 154(b) by 68 days.

(21) Appl. No.: 12/992,494

(22) PCT Filed: May 13, 2009

(86) PCT No.: PCT/FI2009/050389
§ 371 (c)(1),
(2), (4) Date: Nov. 12, 2010

(87) PCT Pub. No.: WO2009/138564
PCT Pub. Date: Nov. 19, 2009

(65) Prior Publication Data
US 2011/0165575 A1    Jul. 7, 2011

(30) Foreign Application Priority Data
May 14, 2008  (FI) ..................................... 20085450

(51) Int. Cl.
*C12Q 1/68* (2006.01)
*C12P 19/34* (2006.01)

(52) U.S. Cl.
CPC ............ *C12Q 1/6851* (2013.01); *C12Q 1/6883* (2013.01); *C12Q 2600/156* (2013.01)
USPC ........................... 435/6.12; 435/6.1; 435/6.11

(58) Field of Classification Search
None
See application file for complete search history.

(56) References Cited

U.S. PATENT DOCUMENTS

| 6,355,422 B1 | 3/2002 | Liu et al. |
| 2003/0087237 A1 | 5/2003 | Hong et al. |
| 2005/0053948 A1 | 3/2005 | Robinson |

FOREIGN PATENT DOCUMENTS

| WO | 02103044 | 12/2002 |
| WO | 2005/026376 | 3/2005 |

OTHER PUBLICATIONS

Pryor et al., "Real-Time Polymerase Chain Reaction and Melting Curve Analysis," Methods in Molecular Biology, 2006, vol. 336, pp. 19-32.*
Hube et al., "Improved PCR Method for Amplification of GC-Rich DNA Sequences," Molecular Biotechnology, vol. 31, No. 1, pp. 81-84 (Sep. 2005).
Liu et al., "Subcycling-PCR for Multiplex Long-Distance Amplification of Regions with High and Low GC Content: Application to the Inversion Hotpot in the Factor VIII Gene," Biotechniques, vol. 25, No. 6, pp. 1022-1028 (Jan. 1998).
Orpana et al., "Multiple Heat Pulses During PCR Extension Enabling Amplification of GC-Rich Sequences and Reducing Amplification Bias," Analytical Chemistry, vol. 84, No. 4, pp. 2081-2087 (Feb. 21, 2012).
Japanese Office Action for Japanese Application No. 2011-508962, filed Jan. 15, 2014.

* cited by examiner

*Primary Examiner* — Young J Kim
(74) *Attorney, Agent, or Firm* — Volpe and Koenig, P.C.

(57) ABSTRACT

The present invention provides a primer extension reaction method, such as a PCR method, for structure-independent amplification of DNA containing CG-rich repeat sequences wherein in the extension step the temperature fluctuates between a first extension temperature and a second extension temperature. The present invention also provides methods for diagnosing disorders. The present invention also provides a thermal cycler programmed to perform the method of the invention.

22 Claims, 10 Drawing Sheets

Fig 1

DM1 samples w/ 180-1800 CTG repeat units.

METHOD FOR SYNTHESIZING DNA STRAND

The sequence listing titled "Sequence_Listing," which was created on Feb. 7, 2011 and had a file size of 517 bytes, is incorporated herein by reference as if fully set forth.

FIELD OF THE INVENTION

The present invention relates to a primer extension reaction method. More particularly the present invention relates to a primer extension reaction method, such as a polymerase chain reaction method, capable of structure-independent amplification of difficult-to-amplify DNA having high content of cytosine and guanosine nucleotides, repetitive sequences and forming strong secondary structures. The present invention also relates to methods for diagnosing disorders such as Dystrophia Myotonica, type 1, Fragile X syndrome and EPM1 by polymerase chain reaction. The present invention also relates to a thermal cycler programmed to perform the method of the invention.

BACKGROUND OF THE INVENTION

Polymerase chain reaction, PCR, has been used for more than two decades to create multiple copies of a segment of the original template DNA, and new applications and modifications emerge every day.

For example U.S. Pat. No. 4,683,202 is one of the earliest patent documents disclosing the PCR method. It describes a process for amplifying at least one specific nucleic acid sequence contained in a nucleic acid or a mixture of nucleic acids wherein each nucleic acid consists of two separate complementary strands, of equal or unequal length, which process comprises: (a) treating the strands with two oligonucleotide primers, for each different specific sequence being amplified, under conditions such that for each different sequence being amplified an extension product of each primer is synthesized which is complementary to each nucleic acid strand, wherein said primers are selected so as to be sufficiently complementary to different strands of each specific sequence to hybridize therewith such that the extension product synthesized from one primer, when it is separated from its complement, can serve as a template for synthesis of the extension product of the other primer; (b) separating the primer extension products from the templates on which they were synthesized to produce single-stranded molecules; and (c) treating the single-stranded molecules generated from step (b) with the primers of step (a) under conditions that a primer extension product is synthesized using each of the single strands produced in step (b) as a template. Since then the method was further developed, for example as described in U.S. Pat. No. 4,800,159 and U.S. Pat. No. 4,965,188, but the basic principal is well known to one skilled in the art.

Also thermal cyclers for carrying out the PCR methods are well-known in the art. For example U.S. Pat. No. 5,038,852 discloses a basic PCR device comprising a heat conducting container for holding a reaction mixture, means for heating, cooling, and maintaining said container to or at any of a plurality of predetermined (user-defined) temperatures and having an input for receiving a control signal controlling which of said predetermined temperatures at or to which said container is heated, cooled, or maintained; and a computer means, coupled to the input of said means for heating and cooling to generate the proper control signals to control the temperature levels, temperature rate-of-change ramps, and timing of the incubations at certain temperature levels.

Although it seems that PCR methods exist for every application, there still remain certain templates PCR cannot handle. Amplification of long fragments was difficult until it was found that DNA polymerases with proof-reading activity could improve long-PCR amplifications (Barnes, W. M. 1994, "PCR amplification of up to 35-kb DNA with high fidelity and high yield from lambda bacteriophage templates", Proceedings of the National Academy of Sciences of the United States of America, vol. 91, no. 6, pp. 2216-2220; Mukai, H. & Nakagawa, T. 1996, "Long and accurate PCR (LA PCR)", Nippon rinsho. Japanese Journal of Clinical Medicine, vol. 54, no. 4, pp. 917-92). However, the amplification efficiency of these enzymes is relatively poor compared with standard non-proof-reading polymerases. For this reason several companies brought into market mixtures of proof-reading and more processive traditional DNA polymerases designed for amplification of long and difficult fragments.

One of the problems people performing PCR amplifications still face very often is how to amplify over CG-rich DNA containing repetitive sequences forming strong secondary structures. Examples of such structures include CG, CTG and GCC repeats. When such structures are formed, there will be only partial extension as it is assumed that the DNA polymerase collides with the double stranded secondary structures. This results in incomplete extension and poor overall amplification efficiency. The incomplete extension relates also to another commonly known phenomenon. If stopped on the repetitive region the partially extended new DNA strand has in its 3' end a stretch of the repetitive sequence. It is released in the next denaturation step, and the 3' end can anneal into any part of the repeat, right or wrong position, and it will be extended in the next extension step. Due to this misalignment and many other reasons related to the experimental conditions, such as DNA polymerase or template DNA concentrations etc. the fragments end up being different in length, which can be seen as a typical smear on the agarose gel.

Disease-causing repeat instability is an important and unique form of mutation that is linked to more than 40 neurological, neurodegenerative and neuromuscular disorders. These repeats consist of multiple, often dozens or hundreds, copies of short, typically less than 10 nucleotides long, repeat units. DNA repeat expansion mutations are dynamic and ongoing within tissues and across generations. The patterns of inherited and tissue-specific instability are determined by both gene-specific cis-elements and trans-acting DNA metabolic proteins. Repeat instability probably involves the formation of unusual DNA structures during DNA replication, repair and recombination. Experimental advances towards explaining the mechanisms of repeat instability have broadened our understanding of this mutational process. They have revealed surprising ways in which metabolic pathways can drive or protect from repeat instability.

Numerous common inherited diseases are caused by expansion of CG-rich repeat sequences (Mirkin, S. M. 2007, "Expandable DNA repeats and human disease", Nature, vol. 447, no. 21, pp. 932-940; Mirkin, S. M. 2006, "DNA structures, repeat expansions and human hereditary disorders", Current Opinion in Structural Biology, vol. 16, no. 3, pp. 351-358). The secondary structures formed in these extended CG-rich repeats have been considered as a major disease mechanism.

The secondary structures and the difficulty to remain in singe stranded state due to the high melting temperature of a CG-rich fragment are the major obstacles blocking DNA polymerase from extending during primer extension. This results in inefficient primer extension and poor amplification efficiency.

The secondary structures are often formed as a result of the self complementary DNA strands searching for their minimum structural energy states. If a secondary structure can be taken as an energy state minimum, one would expect that in fixed conditions the energy minimum would be the same for every molecule of the amplicon and the molecules would finally end up in a similar secondary structure.

However, in long and repetitive fragments the process is more complicated and a one-and-only end structure is not very likely, but rather multiple structures with very similar minimum energy states are found.

Diagnostic analysis of the length of the repeat expansion can be done with many methods. If the expected repeat expansions are relatively short, extension over these repeats is possible. Amplification of these repeat sequences followed by fragment is a routine procedure in diagnostic laboratories. However, in many of the diseases the repeat expansion is too long and/or CG-rich for current PCR methods.

Reliable identification of one copy of an expanded CG-rich repeat causing dominantly inherited diseases or found in unaffected carriers of a recessively inherited disease is especially difficult because of the presence of one copy of unexpanded, short repeat allele. In suboptimal PCR conditions this short wild type allele has much higher amplification efficiency and it often monopolizes the amplification reaction, resulting poor amplification of the expanded allele and a diagnostic error. Inability to reliably amplify over long CG-rich segments has forced diagnostic laboratories to use other technologies, e.g. Southern blotting, to analyze these repeat expansions.

Certain methods have been developed to overcome the problem of amplifying GC-rich regions. Various additives, co-solvents, including DMSO, glycerol and Betaine, have been used to lower the high melting temperature of the CG-rich segments (Henke, W., Herdel, K., Jung, K., Schnorr, D. & Loening, S. A. 1997, "Betaine improves the PCR amplification of GC-rich DNA sequences", Nucleic acids research, vol. 25, no. 19, pp. 3957-3958; Hubé, F., Reverdiau, P., lochmann, S. & Gruel, Y. 2005, "Improved PCR method for amplification of GC-rich DNA sequences", Molecular biotechnology, vol. 31, no. 1, pp. 81-84).

In some methods an analogue of dGTP is used. For example U.S. Pat. No. 5,091,310 discloses a method for structure-independent amplification of DNA by the polymerase chain reaction, said method comprising: (a) treating the DNA under hybridizing conditions with a pair of oligonucleotide primers, a DNA polymerase, dATP, dCTP, TTP, and $c^7dGTP$ such that an extension product of each oligonucleotide primer is formed that is complementary to the DNA, wherein the extension product of a first primer of said primer pair, when separated from its template, can serve as a template for synthesis of the extension product of a second primer of said pair; (b) separating the extension products from the templates on which the extension products were synthesized; and (c) repeating steps (a) and (b) on the extension products produced in step (b). In spite of these additives, long, repetitive and/or CG-rich fragments have often remained "un-PCRable".

U.S. Pat. No. 6,355,422 B1 discloses a method wherein two different constant extension temperatures are used (Liu, Q. & Sommer, S. S. 1998, "Subcycling-PCR for multiplex long-distance amplification of regions with high and low GC content: application to the inversion hotspot in the factor VIII gene", BioTechniques, vol. 25, no. 6, pp. 1022-1028). The authors describe a PCR method for amplification of a large duplication showing GC-rich and CG-poor segments. Because the segment had regions with low GC-content, they used lowered extension temperature of 60° C. together with the more conventional 65° C. A single extension step contained two 2-minutes sessions in both temperatures.

Although human genome is sequenced, the large-scale sequencing projects are frequently struggling with inefficient amplification over areas with CG-rich repetitive segments. This problem is even more pronounced when genomes from other species than human having higher CG-content are studied. There is a need for a PCR method which can overcome this problem. Such a PCR method would be valuable also for example for the diagnosing of diseases and disorders related to such sequences, such as diseases described above. Efficient primer extension over CG-rich sequences would also allow reliable DNA sequencing over CG-rich sequences.

The present invention is based on the surprising discovery that turning PCR reaction from classical PCR amplification using constant denaturation, primer annealing and primer extension temperatures (the last two steps can be combined in 2-step PCR) into a more dynamic process considerably improved the amplification efficiency over the CG-rich repetitive sequences.

Slow, progressive elevation to a much higher primer extension temperatures than are conventionally used resulted in extension over very CG-rich repeat. This, however, was not sufficient to allow efficient amplification over long self complementary CG-rich repeats forming secondary structures.

It appeared that the extension over long CG-rich repeats could be accomplished if the DNA strand was not allowed to settle into a fixed secondary structure, but rather was kept in transition by continuously changing the extension temperature in a pulsate manner. The changing temperature forces the secondary structures to continuously change, and even the strongest secondary structures would eventually, and at least temporarily, open, allowing DNA polymerase to extend a step further. In proper experimental conditions the newly synthesized extending DNA strand maintains its position relative to the template strand although the secondary structures are forced to open. The pulsation also gives DNA polymerase significantly more time to perform the extension at an optimal temperature and the probability of reaching complete extension increases.

The original reason for developing the method of the invention, also called as Heat Push PCR, originated from the need for novel methods for analysis of inherited diseases caused by extensions of CG-rich repeat sequences.

One of the most challenging for PCR amplification has been the diagnostic testing of the Progressive myoclonus epilepsy 1, also known as EPM1 disorder. The major mutation found in Finnish patients is an expansion of a dodecamer repeat (CCCCGCCCCGCG [SEQ ID NO: 1]) in the 5[1] untranslated region of cystatin B (CSTB) gene. The normal alleles usually contain two or three copies of the dodecamer repeat, while the expanded mutant alleles have been reported to contain between 30 and 80 copies. This expansion impairs the promoter function and in homozygous individuals results in the lack of CSTB expression and a severe disease phenotype. EPM1 is recessively inherited; thus affected individuals have two expanded alleles, while unaffected mutation carriers have only one expanded allele. The dodecamere repeat of EPM1 is not symmetric or self complementary, suggesting that it would not make as strong secondary structures as do symmetrical repeats. Thus, difficulties in PCR amplification over the EPM1 expansion could be more related to its extremely high CG-content (nearly 1 kb only C or G nucleotides) than to strong secondary structures.

Dystrophia Myotonica, type 1 (DM1) is an inherited disease caused by an expansion of a CTG repeat in the promoter region of the Dystrophic myotonica protein kinase (DMPK) gene. As in dominantly inherited repeat expansion diseases only one allele is expanded. Unaffected individuals carry 5-34 repeat units while affected patients show more than 50, sometimes over 2000 repeat units. In congenital form of DM1, a large repeat expansion of uniform size is usually found. The expansions are easily detected in Southern blotting assay. The diagnostics of the adult form of DM1 is, on the other hand, sometimes complicated by high cellular length variability of the expanded repeats. If the individual length variability is large, instead of a single band, a smear and/or multiple bands are seen in Southern blotting, severely decreasing the signal to noise ratio of the assay.

Fragile X syndrome (FRAXA) is caused by the expansion of a CGG repeat in the 5' untranslated region of the X chromosomal Fragile site mental retardation 1 (FMR1) gene. The repeat length between 50 and 200 is considered as pre-mutation, an expansion more than 200 repeat units long is considered as a full mutation.

Anticipation, the further expansion of the slightly expanded alleles in next generation is a common problem of inherited diseases caused by repeat expansions. This makes it important also to identify the asymptomatic carriers of the slightly expanded alleles (Pearson C E, Nichol E K, Cleary J D: Repeat instability: mechanisms of dynamic mutations. Nat Rev Genet. 2005 October; 6(10):729-42).

The tissue heterogeneity of repeat lengths, as well as cellular mosaicisms severely hamper the detection of expanded alleles. Sometimes only a fraction of the cells in the sample carry large expansions, and in those cases amplification of the short wild type allele may completely prevent expanded fragments from amplifying when conventional methods are used.

Dystrophic Myotonia, type 1, DM1 was chosen as the primary model system for the method of the present invention for the following reasons:

- Being a dominantly inherited disease, the affected patients have one unexpanded allele and one expanded allele.
- The CTG repeat expansion can be over 1000 repeat units long and in a sample one can have multiple variable expanded fragments.
- No PCR protocols exist for efficient amplification over long repeat expansions.
- Southern blotting analysis allowed direct estimation of the repeat expansion length and its variability in the original samples. Thus, amplification efficiency could be estimated not only between an expanded and an unexpanded allele, but also between multiple expanded fragments differing slightly in size.

To demonstrate the robustness of the method of the present invention, another, clinically very important inherited disease, the Fragile X syndrome, was chosen. The CGG repeat forms strong secondary structures and is considered one of the most difficult fragments to amplify.

BRIEF DESCRIPTION OF THE INVENTION

The present invention provides a primer extension reaction method, such as a polymerase chain reaction (PCR) method, for structure-independent amplification of DNA comprising preparing a reaction mixture containing the sample DNA, primers, one or multiple enzymes capable of synthesizing a nucleic acid strand complementary to the original nucleic acid strand, such as a thermostable DNA polymerase, mixture of dNTPs and a buffer, denaturing the DNA in a denaturation step, annealing the primers in an annealing step, extending the annealed primers in an extension step, wherein in the extension step the temperature first rises from the annealing temperature to first, lower, extension temperature in the range of 70-90° C., then fluctuates up to second, higher, extension temperature in the range of 75-95° C. and back down to the first extension temperature for a plurality of cycles to destabilize the secondary structures in the DNA to allow the extension. This up and down pulsate change in the extension temperature can be performed using repeated cycling between two or more temperatures. In one embodiment the steps are repeated for a plurality of cycles to obtain amplified DNA. The present invention also provides a thermal cycler programmed to perform the method of the present invention. Preferably said thermal cycler can be programmed to perform a large amount of pulses, for example 100 or more.

The present invention further provides a computer-readable data storage medium having a computer-executable program code stored operative to perform the method of the present invention.

The present invention also provides methods for diagnosing diseases or disorders related to DNA containing repeat sequences forming secondary structures wherein the primer extension method of the invention is used to amplify said DNA for diagnostic purposes.

The present invention also provides a method for diagnosing progressive myoclonus epilepsy 1 (EPM1), wherein the method of the invention is used to amplify the EPM1-specific DNA to allow the analysis of the number of repeat units in said DNA to make diagnosis.

The present invention also provides a method for diagnosing Fragile X syndrome, wherein the method of the invention is used to amplify the Fragile X syndrome-specific DNA to allow the analysis of the number of repeat units in said DNA to make diagnosis.

The present invention also provides a method for diagnosing Dystrophia Myotonica, type 1, wherein the method of the invention is used to amplify the Dystrophia Myotonica, type 1-specific DNA to allow the analysis of the number of repeat units in said DNA to make diagnosis.

The method of the present invention showed improved amplification efficiency to amplify the fragments irrespective of the length of the repetitive CG-rich segments demonstrating its usefulness in balanced and efficient amplification of long and CG-rich repeat sequences.

It is the advantage of the present invention that DNA sequences having high melting temperature and/or problematic secondary structures can now be amplified efficiently. This will make it possible to amplify certain DNA sequences that were impossible or very difficult to amplify before. This further allows sophisticated diagnostic methods utilizing PCR methods and thus also diagnosing certain diseases and disorders that were difficult to diagnose or recognize before.

DETAILED DESCRIPTION OF THE INVENTION

Definitions

The term "CG-rich repeat" refers to a segment of genome comprising a short repeat unit (generally <20 nucleotides long) in which more than 60% are either C or G. This repeat unit is generally replicated uninterrupted more than three times, often tens or hundreds of times.

The term "expanded repeat" means that a repeat unit is replicated uninterrupted more than three times, often tens or hundreds times. The repeat number in affected individuals is higher than found in general population. It can be a pre-mutation or a full mutation.

The term "Heat Push" means that temperature fluctuates multiple times between the first and the second extension temperatures. The rate of heating and cooling may differ and there may be additional temperature turning points between the first and second extension temperatures. This temperature fluctuation between the first and the second extension temperatures is replicated plurality of times, generally more than three times, for example 20-40 times, up to hundreds of times during a PCR cycle. Depending on the target and experimental conditions, one must optimize the use of lower number of pulses with slower heating rates or a higher number of faster pulses.

The term "temperature" refers to the temperature value programmed into the thermo cycler software. Thermo cyclers transfer the temperature by forming a temperature gradient between the block and the liquid in the vessel. It depends on the instrument and predicted ramping rate. Also the programmed reaction volume value affects the formation of these thermal gradients. By programming the reaction volume smaller it is to some extent possible to decrease this feature.

Secondary Structures of CG-Rich Repeat Expansions

Generally it is assumed that the secondary structures of the single-stranded template with CG-rich repeat will stop the DNA polymerase and prevent the primer extension reaction to reach the end of the template strand. The DNA polymerase is able to extend only a part of this CG-rich repeat region before it is stopped by the strong secondary structures. At the denaturation step of the next cycle of a conventional PCR reaction the partly extended and template strands dissociate. During the next annealing step this partially extended strand will re-anneal to a single stranded template DNA. This, however, has two major problems. If the extension has reached the repeat region, re-annealing of the 3' end can take place anywhere in the repeat region, especially if the repeat region is hundreds of bases long. This shifting along the template strand results in variability in the length of the newly synthesized strands. The variability will get stronger during the following PCR cycles, as the strands with repeat length variability will serve as templates for the subsequent PCR cycles. Smearing and stuttering is seen when the amplification products are analyzed on gel electrophoresis and exact estimation of the original repeat length gets very difficult.

Short Expansions are Amplified with Higher Efficiency than Long Ones

Another problem relates to the poor amplification efficiency if multiple PCR cycles are needed before one complete extension is reached. Sometimes PCR product of a CG-rich repeat expansion is formed, although with very poor efficiency, if the expanded allele is present alone. In heterozygous or mosaic samples having also shorter template DNAs, expansion of similar size is not amplified. The reason for this is that an allele with very short repeat region is amplified with significantly higher amplification efficiency, and the short allele monopolizes the amplification reaction. The expanded allele will be amplified very poorly. Due to the poor amplification efficiency, one has been using Southern Blotting for detection of PCR product from expanded alleles (Gennarelli, M., Pavoni, M., Amicucci, P., Novelli, G. & Dallapiccola, B. 1998, "A single polymerase chain reaction-based protocol for detecting normal and expanded alleles in myotonic dystrophy", Diagnostic molecular pathology: the American journal of surgical pathology, part B, vol. 7, no. 3, pp. 135-137, Brugnoni R, Morandi L, Briscioli V, Cornelia F, Mantegazza R: A new non-radioactive method for the screening and prenatal diagnosis of myotonic dystrophy patients. J Neurol (1998) 245:289-93).

Amplification Over CG-Rich Sequences by Single Heating Step PCR

The high content of C and G nucleotides raises the melting temperature of the double stranded DNA. High CG-content has been a common and well known problem of PCR amplification from its beginning. Obviously, simply using a higher extension temperature alone is not successful; otherwise amplification over CG-rich sequences would be a simple routine today.

Figure 1:
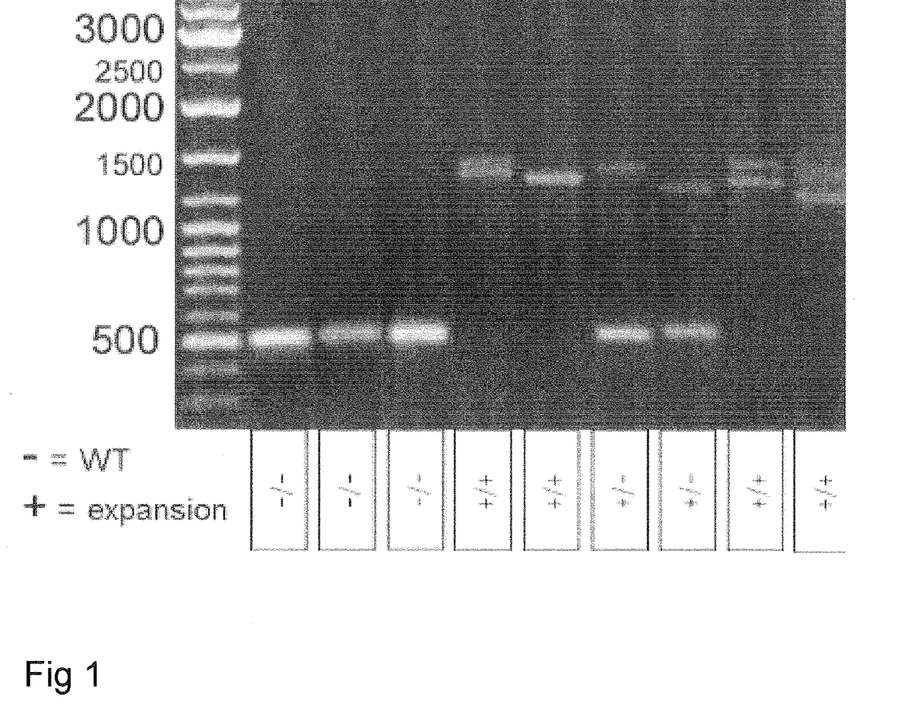
FIG. 1 shows an agarose gel of the results from a single heating step PCR analysis of EPM1 samples. −=wild type, +=expanded dodecamere repeat.
Figure 2:
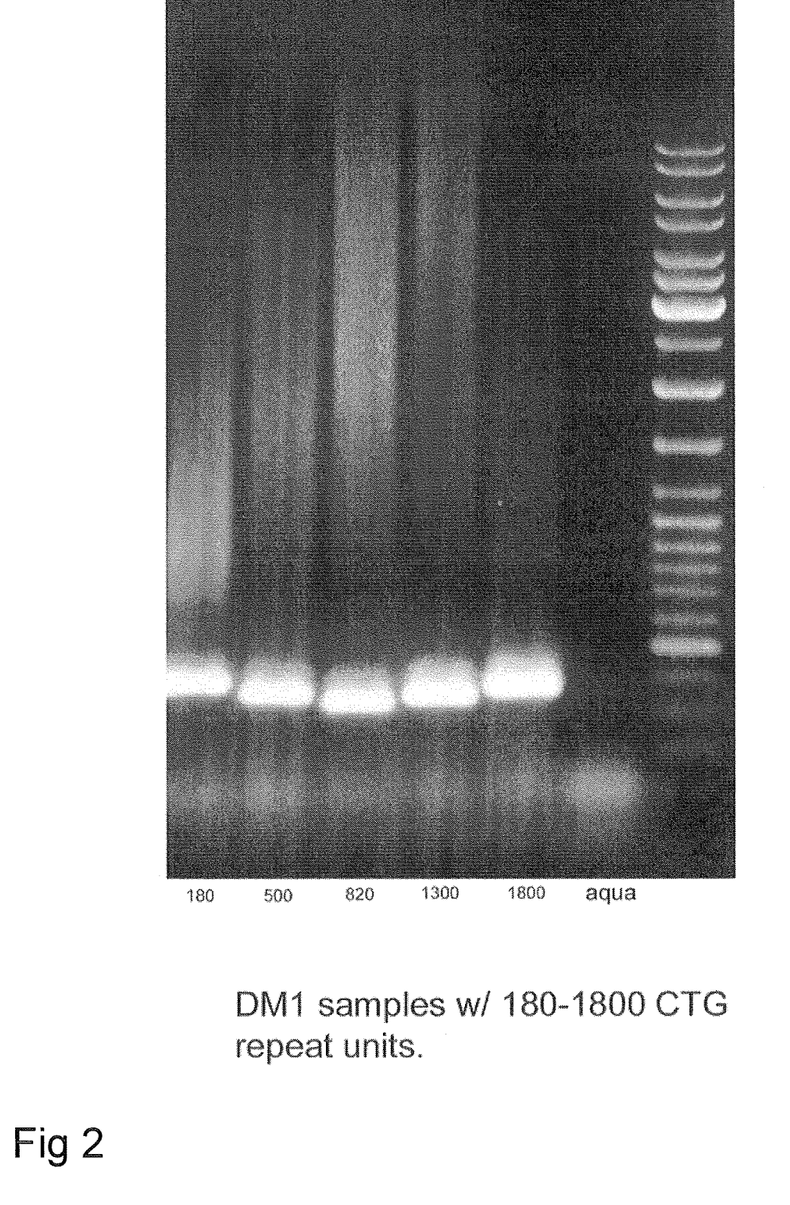
FIG. 2 shows an agarose gel of the results from a single heating step PCR analysis of DM1 samples. The number of (CTG) repeat units detected in Southern Blotting analysis is shown on the X axis. Severe smearing is seen.

In one embodiment of the present invention containing a single heating step PCR the primer extension temperature continuously raises, very slowly, the final temperature being higher than used in conventional PCR, up to 80° C. As the result of this progressive heating the DNA polymerase is able to extend over the expanded EPM1 dodecamere repeat, nearly 1000 bases with 100% CC-content and the PCR products are detected on ethidium bromide stained agarose gel electrophoresis (FIG. 1). The amplification efficiency was so high, that the expanded allele was amplified in the presence of a short unexpanded allele. As the dodecamere repeat is not self-complementary, the difficulties related to PCR amplification of the EPM1 repeat are merely caused by the high CG content and not by strong secondary structures. Amplification over expanded DM1 repeat in comparable conditions results in severe smearing on agarose gels (FIG. 2).

Improved Amplification Efficiency with Heat Push PCR

The Heat Push method of the present invention significantly corrects this difference in amplification efficiencies over short and long CG-rich repeats forming secondary structures.

Unlike in conventional constant temperature extension, or in a single heating step PCR, the thermal pulsation of Heat Push PCR causes the newly synthesized partially extended strand to continuously slightly dissociate and re-anneal to the template, but in such a way that all the time sufficient binding remains between the template and synthesized strand preventing the strand from slipping and losing its position. During pulsing between the lower and upper temperature phases the DNA polymerase is able to extend over the next available free single stranded segment, until it is stopped again by the next secondary structure. Raising the temperature again slowly melts this stopper structure and the extension may continue for a while. This is repeated multiple times during a single primer extension step, and as a result a large proportion of these extensions, step-by-step, reach complete extension length. It is of the utmost importance that the strands do not separate too much during extension, because when the newly synthesized strand does not loose its position relative to the template strand, a complete and accurate copy of the template strand is created. This results in high amplification efficiency and appears to allow efficient simultaneous amplification of both long and short CG-rich repeats.

In spite of years of testing none of the classical PCR methods have been able to efficiently amplify over CG-rich repeats forming strong secondary structures. These classical methods are, however, very different from the present invention, in which the extension temperature fluctuates between lower and upper extension temperatures (e.g. between 76° C. and 83° C.) with virtually no incubation at constant temperatures. This rapid cycling is preferably repeated >20 times (currently limited by the memory of the thermo cycler model used) during a single "extension step". In each case a proper balance between the rate of heating (which increases the time needed to reach the second extension temperature) and the number of extension pulses must be found. Both factors affect the overall assay time.

Previous studies have tried to use different extension temperatures for long-distance amplification of regions with high and low CG content. In the Subcycling method, described in U.S. Pat. No. 6,355,422 (Liu, Q. & Sommer, S. S. 1998, "Subcycling-PCR for multiplex long-distance amplification of regions with high and low GC content: application to the inversion hotspot in the factor VIII gene", BioTechniques, vol. 25, no. 6, pp. 1022-1028) two different extension temperatures, 60° C. and 65° C., 2 minutes each, were used. It allowed extension over of the CG-rich and AT-rich segments of the inversion duplication of intron 22 of X chromosomal factor VIII gene. This genomic structure is not a self complementary CG-rich repeat forming strong secondary structures.

Comparisons to existing methods are hampered by nearly complete lack of publications on efficient amplification of long CG-rich repeats using conventional PCR. The reason for this might be that strand replacement activity of the current DNA polymerases is not capable of amplification over CG-rich repeat structures forming strong secondary structures.

The method of the present invention thus provides a primer extension reaction method, such as a polymerase chain reaction (PCR) method, with improved structure-independency for amplification of DNA. The method especially allows the amplification of DNA which contains sequences or segments having very high GC content and/or causing the formation of DNA secondary structures. Non-limiting examples of such structures include CG, CTG and GCC-rich repeats.

The invention is described herein mainly referring to a PCR method wherein there is a plurality of amplification cycles. However, all such methods having one or more of such cycles are in the scope of the invention. Besides the PCR method, in one embodiment the present invention provides a method for sequencing DNA by using the primer extension reaction of the invention. In another embodiment the present invention provides a method for preparing labeled DNA fragments for hybridization assays by using the primer extension reaction of the invention.

In the method of the present invention a conventional primer extension reaction mixture may be utilized generally containing at least the sample DNA, primers, one or multiple enzymes capable of synthesizing a nucleic acid strand complementary to the original nucleic acid strand, such as a thermostable DNA polymerase, mixture of dNTPs, a buffer and possibly co-solvents and the like. The preparation of such reaction mixtures are well known to a person skilled in the art.

The method of the present invention comprises denaturing the DNA in a denaturation step, annealing the primers in an annealing step, extending the annealed primers in an extension step, and, in the case of PCR, repeating the steps for a plurality of cycles to obtain amplified DNA. Also these steps are included in most of the conventional PCR methods and are known to a person skilled in the art.

Characteristic of the method of the present invention is that in the extension step after the temperature has first risen from the annealing temperature progressively to the first lowest extension temperature, it then fluctuates gradually up to second or more, higher extension temperature(s) and back down to the first lowest extension temperature for a plurality of cycles to destabilize the secondary structures in the DNA to allow the extension. In practice there is substantially no incubation at constant temperatures during the extension. This fluctuation of the extension temperature can be done using two or more temperatures and heating or cooling rates. Separate annealing step can also be omitted.

The difference between the lowest extension temperature and the highest extension temperature should be enough to maintain the annealing of the extending new DNA strand and prevent the template DNA from settling into a strong fixed secondary structure when the temperature fluctuates up and down. This may also depend on the fluctuation rate. Typically the first lowest extension temperature may be in the range of 70-90° C. In one embodiment the lowest extension temperature is in the range of 70-78° C. In another embodiment the lowest extension temperature is in the range of 76-78° C. The second highest (higher than the first extension temperature) extension temperature may be in the range of 75-95° C. In one embodiment the highest extension temperature is in the range of 80-83° C. Generally the difference between the first and the second extension temperature is in the range of 1-20° C., preferably 3-10° C. There may be also other low and high temperatures used between said lowest and highest temperatures.

The fluctuation cycle between the lowest and the highest extension temperatures is repeated more than 3 times in each extension step. The balance between optimal rate of heating and the number of extension pulses depends on the experimental conditions. Generally 20-40 cycles are used, but depending on the capacity of the PCR device even hundreds of cycles are possible.

In one embodiment in the extension step the heating and cooling rates are in the range of 0.01-10° C./s, preferably in the range of 0.01-1° C./s, such as about 0.1° C./s. In one embodiment such controlled heating rate is used when rising the temperature and the cooling is carried out as fast as possible.

In one embodiment the reaction mixture contains co-solvents, such as DMSO, glycerol or Betaine. By adding co-solvent, such as Betaine, lower extension temperatures may be used. Usually about 1.8 mol/l Betaine was used in the experiments, but the amount may be for example in the range of 0-3 mol/l, generally 1-2 mol/l.

The present invention also provides a thermal cycler programmed to perform the method of the present invention. The thermal cycler may be any suitable thermal cycler containing the essential elements of a PCR device as it is known in the art, such as the computer means for generating the proper control signals to control the temperature levels, temperature rate-of-change ramps, and timing of the incubations at certain temperature levels. The computer means may be integrated in the cycler.

The present invention further provides a computer-readable data storage medium having a computer-executable program code stored operative to perform the method of the present invention. Such data storage medium may be used to provide the program to the computer means of a thermal cycler to operate the cycler in a PCR method.

Generally the present invention provides methods for diagnosing diseases or disorders related to DNA containing extended CG-rich repeat sequences forming secondary structures wherein the PCR method of the invention is used to amplify said DNA for the diagnostic purposes. In one embodiment the diagnostic method is electrophoretic fragment analysis. Also other methods for making diagnoses or other non-diagnostic methods involving DNA amplification may be used, such as sequencing methods, quantitative PCR (qPCR), reverse transcription PCR (RT-PCR) or the like. In one embodiment said PCR uses a complementary DNA as the template. A person skilled in the art knows these methods and can apply the method of the invention to them.

In one embodiment the present invention also provides a method for diagnosing progressive myoclonus epilepsy 1 (EPM1). In one embodiment the PCR method of the invention is used to amplify the EPM1-specific DNA to allow the analysis of the number of repeat units in said DNA to make diagnosis.

In another embodiment the present invention also provides a method for diagnosing Fragile X syndrome. In one embodiment the PCR method of the invention is used to amplify the Fragile X syndrome-specific DNA to allow the analysis of the number of repeat units in said DNA to make diagnosis.

In still another embodiment the present invention also provides a method for diagnosing Dystrophia Myotonica. In one embodiment the PCR method of the invention is used to amplify the Dystrophia Myotonica-specific DNA to allow the analysis of the number of repeat units in said DNA to make diagnosis.

EXAMPLES

PCR Design

It is important not to position the primers used in present invention too close to the actual repeat. If possible, the primers should be positioned so that some CG-rich stretches would also be included in the short wild type allele to balance the amplification efficiencies. The primers are longer than usual and located in relatively CG-rich segments, resulting in conditions where primers anneal at a relatively high temperature, so that the DNA polymerase would initiate primer extension immediately. In one embodiment PCR additive Betaine is included in the PCR.

Single Heating Step PCR Program

It was found that relatively short CG-rich repeats (<1 kb) could be amplified with a single, very slow heating-extension step. The extension temperature was set to rise gradually and very slowly from the annealing temperature up to 80° C.

In the presence of 1.8 M Betaine, full extension of both short wild type and the expanded EPM1 alleles with 80 dodecamere repeats could be achieved during a single slow progressive heating step. In such a high Betaine concentration pushing with heat during extension apparently was able to open all secondary structures that have prevented conventional PCR amplification of the expansion alleles (FIG. 1).

When similar PCR conditions were used for amplification of long DM1 repeats, stuttering and polymerase slippage was observed, resulting in smearing of the amplification products on agarose gels. Long DM1 expansions could not be amplified (FIG. 2).

Heat Push PCR Program of the Present Invention

Figure 9:
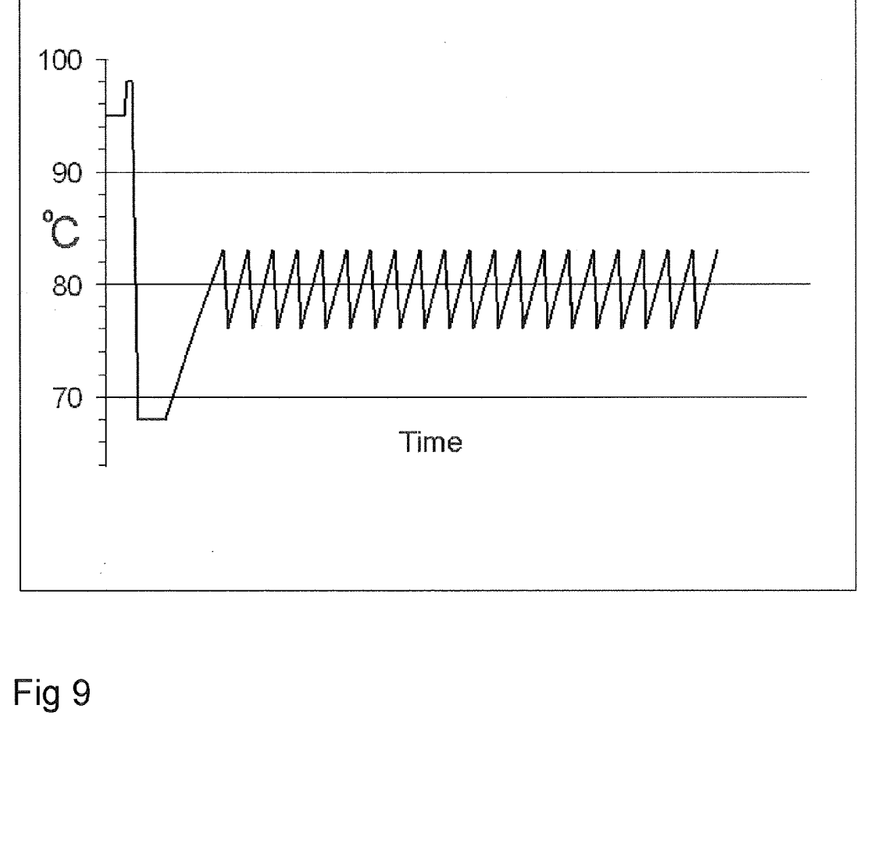
FIG. 9 shows a schematic view of an example of the Heat Push method of the present invention. The initial denaturation and final extension steps are not shown. First in the denaturation step the temperature rises up to a denaturing temperature, such as first to about 95° C. for 45 seconds and then to about 98° C. for 10 seconds. Then the temperature lowers to about 68° C. for 45 seconds at the annealing step. After that the characteristic extension step of the invention starts. The extension temperature fluctuates between the first extension temperature (here about 78° C.) and the second extension temperature (here about 83° C.) for plurality of times. The whole cycle is repeated several times.
Figure 10:
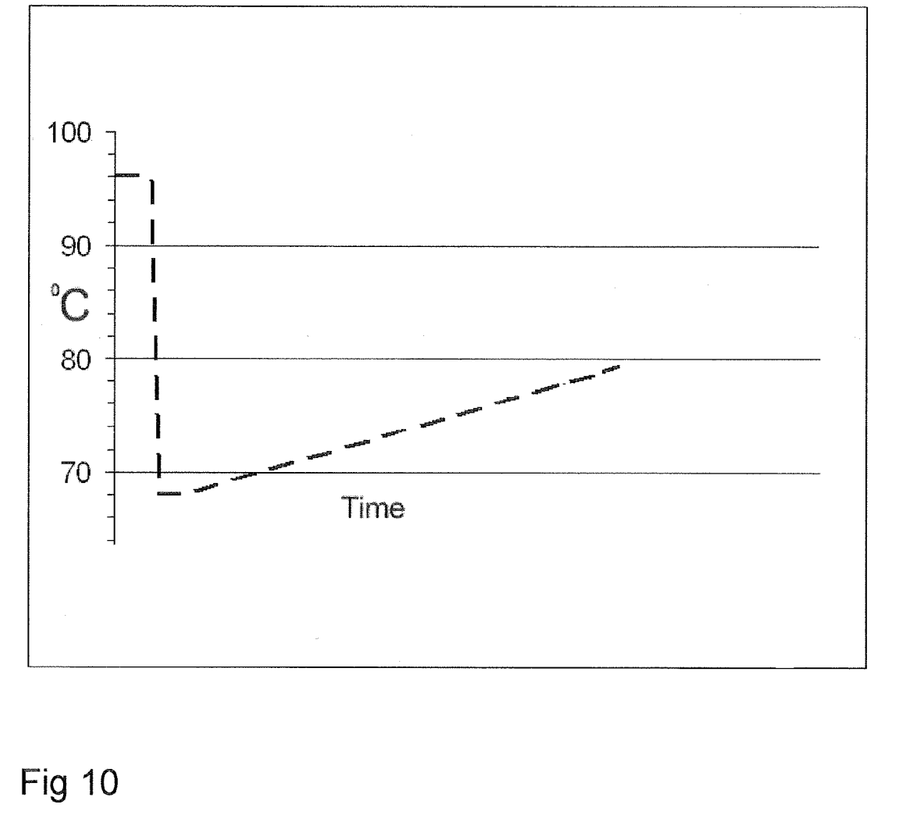
FIG. 10 shows a schematic view of an example of the single heating step PCR method of the present invention. The initial denaturation and final extension steps are not shown. First, in the denaturation step the temperature rises up to a denaturing temperature, such as about 96° C. for 45 seconds. Then the temperature lowers to about 69° C. for 45 seconds at the annealing step. After that the characteristic extension step of the invention starts. The extension temperature rises very slowly to the first and final extension temperature (here about 79° C.). The whole cycle is repeated several times.

Unlike in conventional PCR where the extension temperature remains constant during the whole extension step, in Heat-Push PCR method of the present invention the extension temperature continuously fluctuates. In one non-limiting experiment (see FIG. 9) the programmed denaturation step was first 45 sec at 95° C., then 98° C. for 10 sec. Annealing step was 68° C. for 30 sec, then the extension started by heating to 78° C. followed by multiple progressive heating and cooling steps. The Heat-push pulses comprised slow elevation (about 0.1° C./s.) from 78° C. up to 83° C. and then fast drop back to 78° C. These heating pulses were repeated 21 times during a single PCR cycle. The number of Heat-Push pulses was limited by the memory of the thermo cycler (GeneAmp PCR System 9700, Applied Biosystems) limiting the number of program steps programmable for a cycle.

Figure 3:
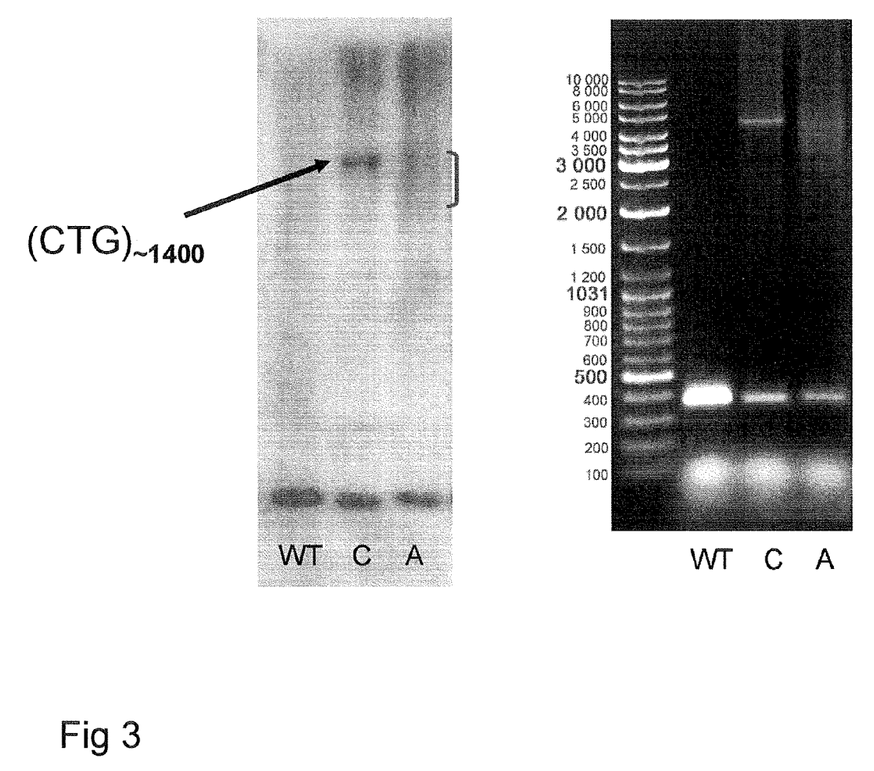
FIG. 3 shows a Southern blotting result (left) from DM1 samples. The unamplified sample DNA from the patient with the adult form (but not with the congenital form) of DM1 contained multiple fragments with slightly different CTG expansion lengths. These fragments were amplified using the Heat-Push method, resulting in a very similar profile on agarose gel (right). WT=wild type, C=congenital DM1, A=adult DM1. Smearing is negligible.

Destabilizing the DNA secondary structures by continuously pulsing the extension temperature made it possible to extend over long CG-rich repeats. Apparently, periodic lower temperature preserved sufficient annealing of the extended fragment with the template while the heating pulse destabilized secondary structures of the template strand, allowing extension with negligible stuttering. Repeating this fluctuating extension over 20 times during a single PCR extension step resulted in such a high extension efficiency that in the sample containing one short wild type allele and one expanded allele containing about 1400 CTG repeats, both alleles were amplified with nearly equal amplification efficiencies. As shown in the Southern blotting result, the unamplified sample DNA contained multiple fragments with slightly different CTG expansion lengths, and these fragments were amplified in a very similar profile when using the method of the invention (FIG. 3).

Figure 4:
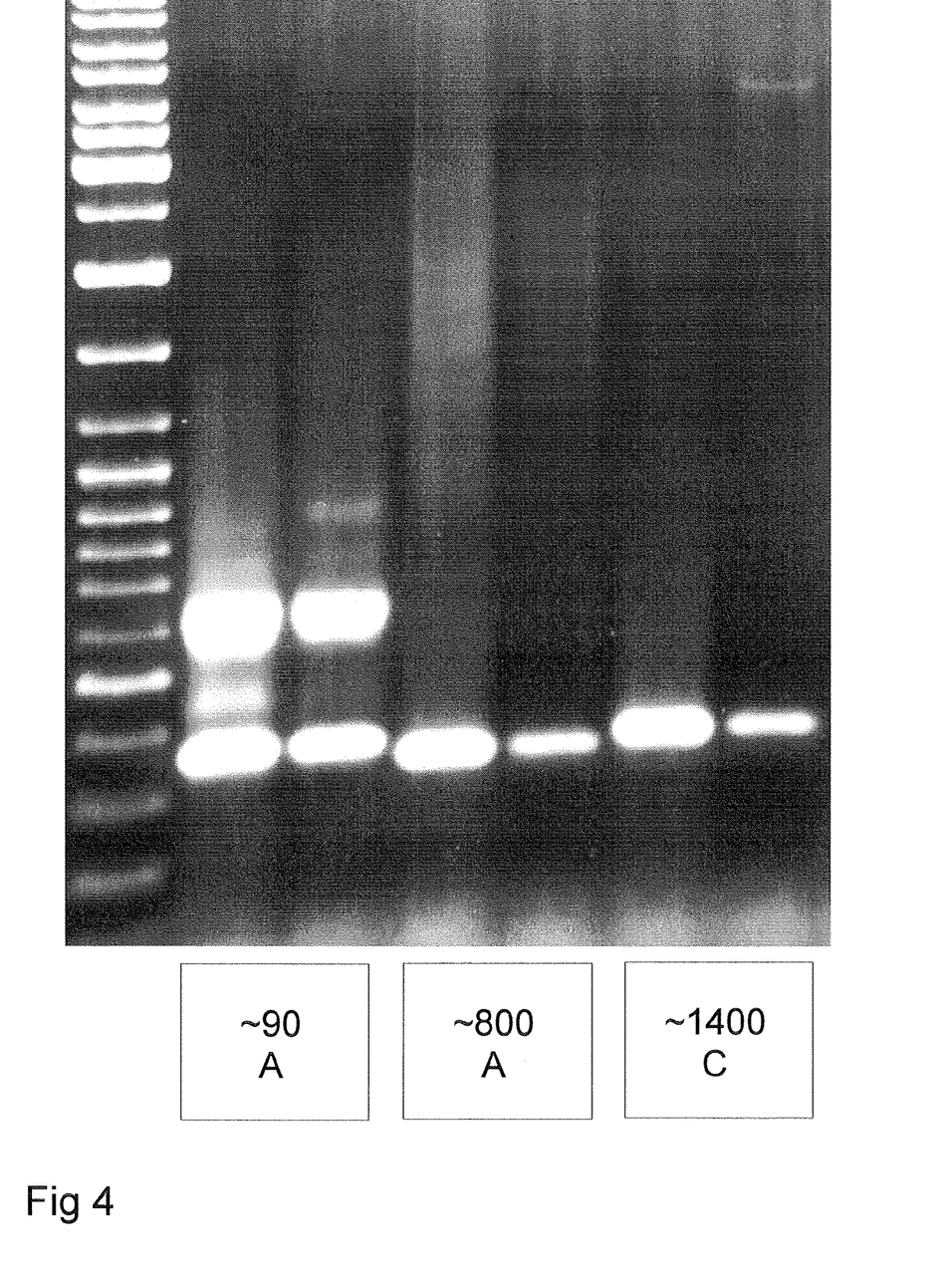
FIG. 4 shows an agarose gel of the results from a simultaneous comparison of the single heating step PCR and the method of the invention. Analyses of DM1 samples. ~n refers to number of (CTG) repeat units, C=congenital DM1, A=adult DM1. On each different sample the first line corresponds to single heating step (SH) results and the second line to the Heat-Push (HP) results. Smearing is negligible in samples amplified with Heat-Push PCR.

The difference in amplification efficiencies between the single heating step PCR (optimized as much as was found possible) and the Heat-Push method is shown in FIG. 4. Samples (40 ng) with small, medium or large DM1 CTG expansions were analyzed. The amplification products of the single heating step PCR showed very similar products from the small expansion. Loss of amplification efficiency, seen as preferential amplification of the wild type allele, and smearing and lack of sharp bands is seen when the sample with medium size expansion is analyzed. The smearing becomes a major problem if the template amount is larger (FIG. 6) or the expansion is longer. The sample with large congenital DM1 is misdiagnosed as PCR over the repeat was unsuccessful. The Heat-Push method of the present invention, on the other hand, showed significantly improved balance in the amplification over the short and long expansions. The amplification product from the medium size adult DM1 shows tissue heterogeneity, but distinct bands are seen. As seen in FIGS. 3 and 4, a single nearly 5 kb PCR product is obtained from the studied congenital DM1 sample.

Figure 5:
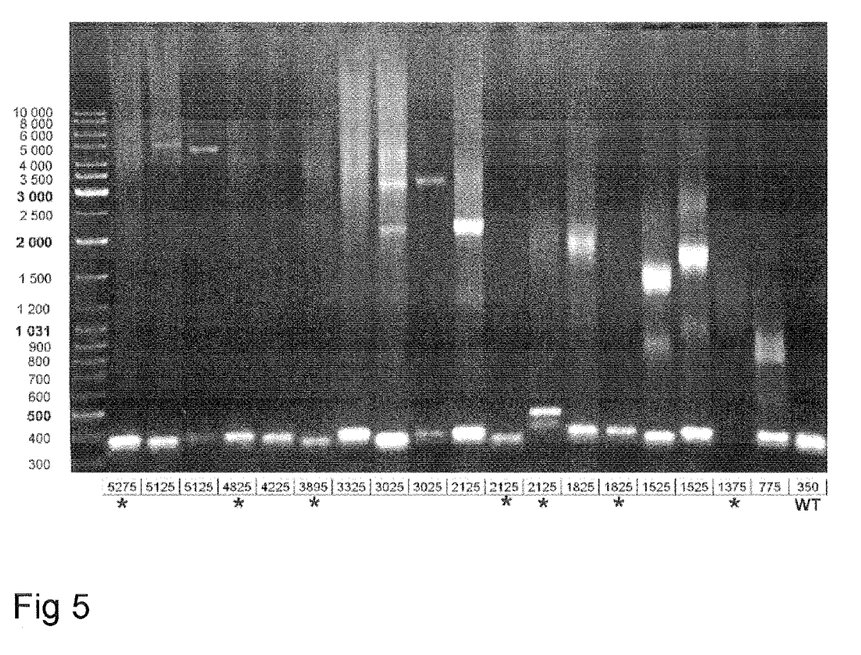
FIG. 5 shows an agarose gel of the results from DNA samples amplified using the DM1 Heat-Push method. The boxed number on the X-axis shows the expected size of the PCR product calculated using the repeat size detected by Southern blotting.

The DNA samples previously analyzed for the length of the DM1 repeat expansion were analyzed by the PCR method of the present invention. The predicted size of the Heat-Push PCR was calculated and shown in a box under each product (FIG. 5). In the validation phase of the assay 78 samples were analyzed and correctly genotyped.

Figure 6:
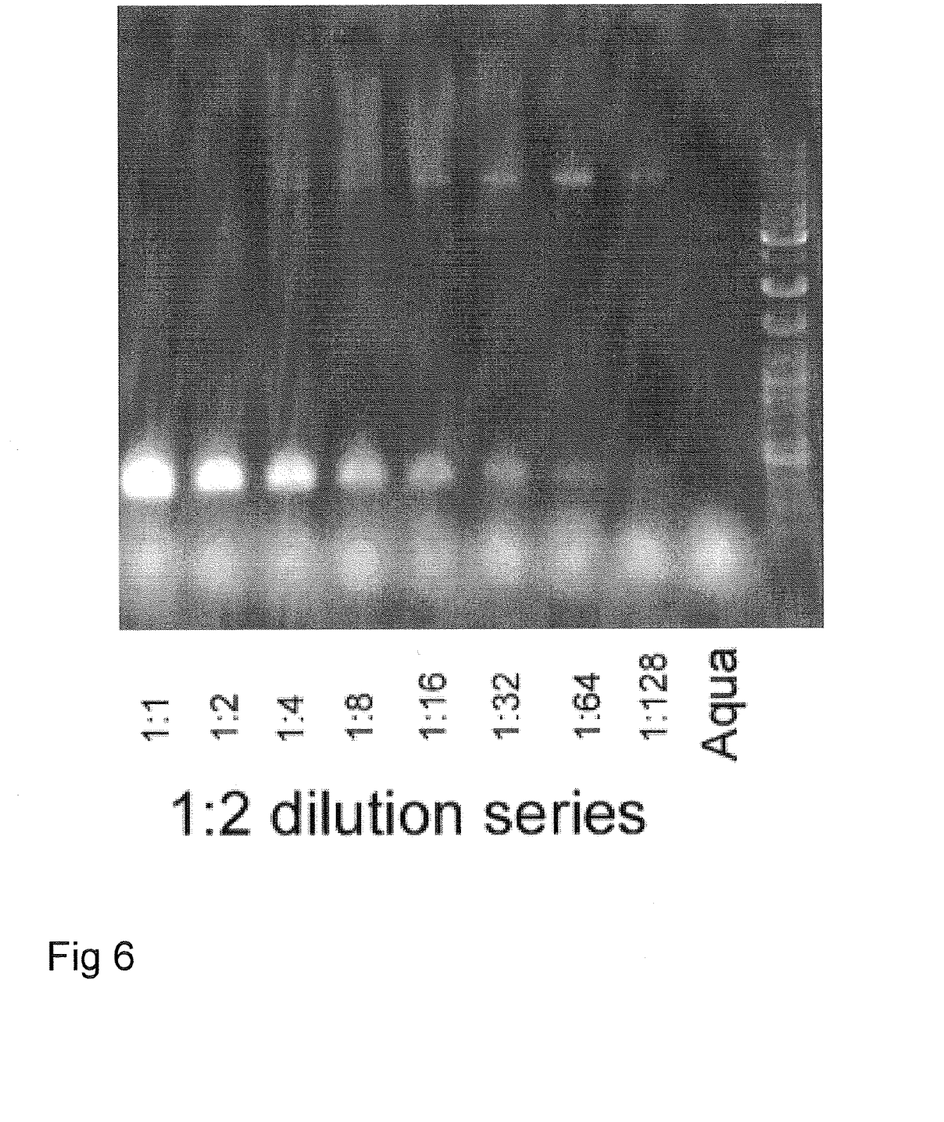
FIG. 6 shows an agarose gel of the results from a dilution series experiment. Dilutions of a DNA sample with a large DM1 CTG repeat expansion was amplified using the DM1 Heat-Push method. Too much template DNA prevents the expanded allele from amplifying.

The success of amplification of an expanded allele is dependent on the quality and quantity of the template DNA. If too much template DNA is used, the expanded allele will amplify poorly (FIG. 6).

Figure 7:
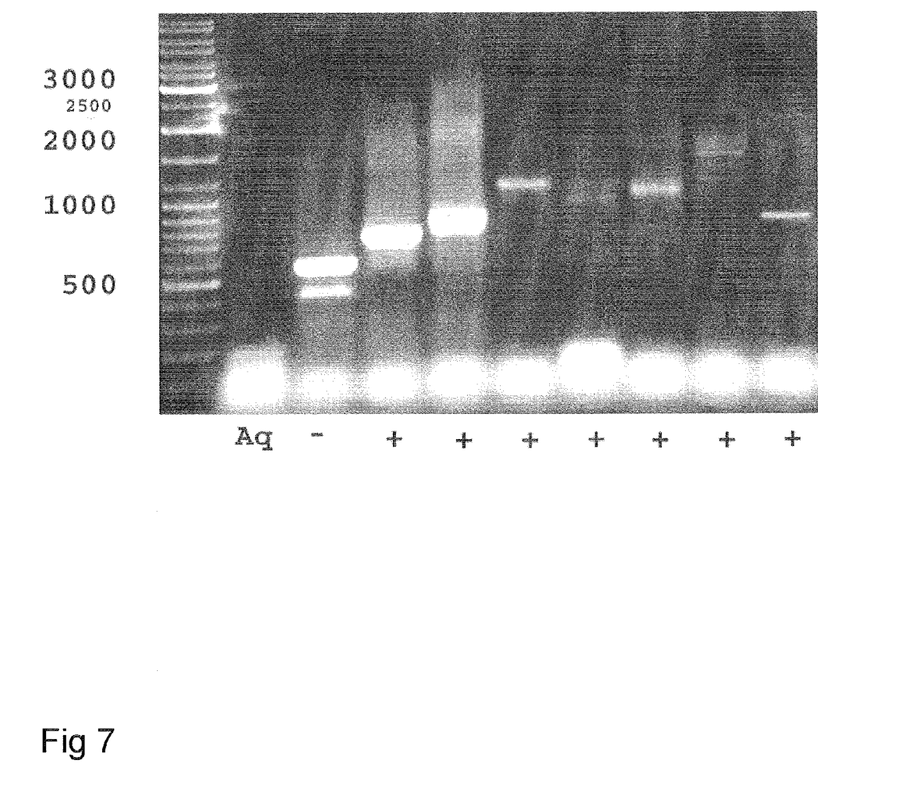
FIG. 7 shows an agarose gel of the results from the Heat-Push (HP) amplification of sample DNAs from males with various number of Fragile X (CGG) repeat units. Aq=Blank, −=wild type, +=expanded (CGG) repeat.

The method of the present invention could also be used for analysis of the CCG expansion of Fragile X, which is considered as one of the most difficult repeat structures for PCR to amplify (FIG. 7).

Figure 8:
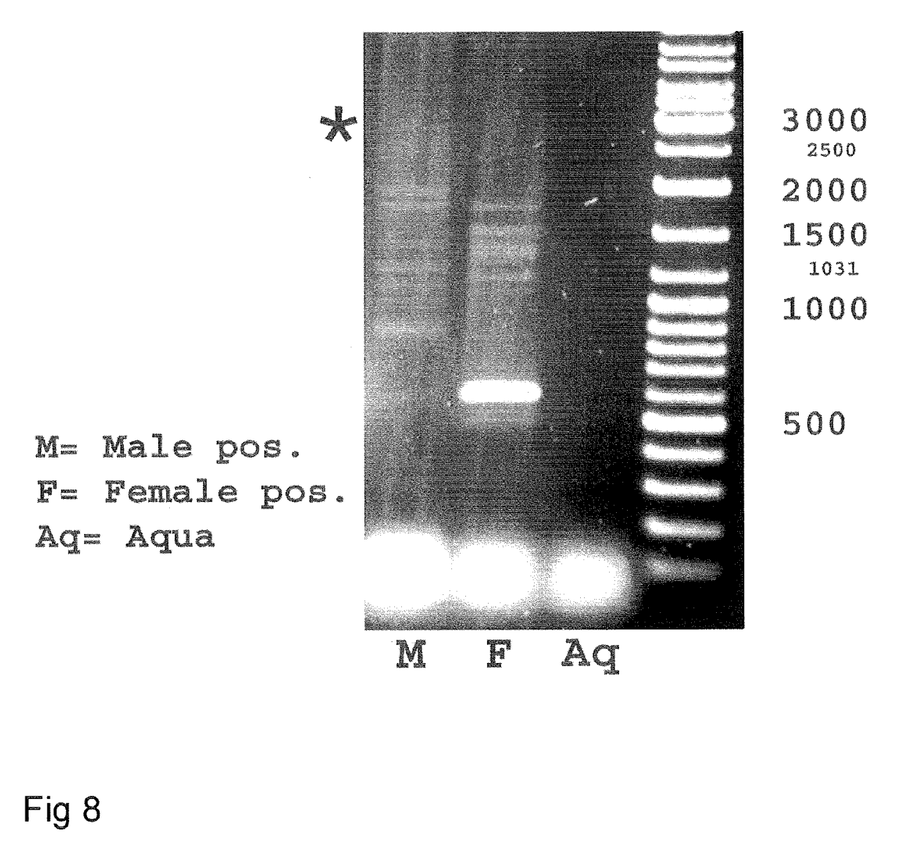
FIG. 8 shows an agarose gel of the results from the Heat-Push (HP) amplification of Fragile X (CGG) sample DNAs from a male (expanded repeats) and a female (multiple expanded repeats and one unexpanded repeat).

The Fragile X samples have larger variability in fragment sizes, and the CCG repeat is very prone to secondary structures, and it has a very high melting temperature. Distinct bands up to nearly 3 kb in size were obtained from samples from males having only one X chromosome, and the presence of one unexpanded repeat in a sample from a female did not prevent expanded fragments from amplifying (FIG. 8).

Mosaicism, expansion length heterogeneity and presence of short wild type alleles are all found in both DM1 and Fragile X samples. Use of Heat-Push PCR significantly improved the balance of amplification between short and long repeats.

The invention claimed is:

1. A primer extension reaction method for structure-independent amplification of DNA comprising:
   preparing a reaction mixture containing sample DNA having CG rich repeats, primers, one or multiple enzymes capable of synthesizing a nucleic acid strand complementary to the sample DNA, a mixture of dNTPs, and a buffer,
   denaturing DNA in the reaction mixture at a denaturing temperature in a denaturation step,
   annealing the primers at an annealing temperature in an annealing step,
   extending the annealed primers in an extension step to obtain amplified DNA, wherein in the extension step includes raising the temperature from the annealing temperature to a first lower extension temperature in the range of 70-90° C., then fluctuating the temperature up to a second higher extension temperature in the range of 80-95° C. and back down to the first lower extension temperature for a plurality of fluctuation cycles to destabilize the secondary structures in the DNA to allow the extension, and wherein the difference between the first extension temperature and the second extension temperature is in the range of 3-10° C.

2. The method of claim 1, wherein the denaturation step, annealing step, and extension step are repeated for a plurality of cycles.

3. The method of claim 1, wherein the first lower extension temperature is in the range of 70-78° C.

4. The method of claim 3, wherein the first lower extension temperature is in the range of 76-78° C.

5. The method of claim 1, wherein the second higher extension temperature is in the range of 80-83° C.

6. The method of claim 1, wherein the plurality of fluctuation cycles between the first extension temperature and the second higher extension temperature includes at least 3 fluctuation cycles.

7. The method of claim 1, wherein in the extension step, fluctuating the temperature occurs at a fluctuation rate selected from the group consisting of in the range of 0.01-10° C./s, in the range of 0.01-1° C./s, and about 0.1° C./s.

8. The method of claim 1, wherein the sample DNA contains GC, CTG or GCC-rich repeats.

9. The method of claim 1, wherein the reaction mixture contains co-solvents.

10. The method of claim 9, wherein the co-solvents include DMSO, glycerol or Betaine.

11. A polymerase chain reaction method comprising amplifying DNA by the primer extension reaction of claim 1.

12. The polymerase chain reaction method of claim 11, wherein it is a quantitative PCR method or reverse transcription PCR.

13. A method for diagnosing diseases or disorders related to DNA containing repeat sequences forming secondary structures comprising amplifying said DNA for the diagnostic purposes by the polymerase chain reaction method of claim 11.

14. The method of claim 13, wherein the disease is Fragile X syndrome.

15. The method of claim 13, wherein the disease is Dystrophia Myotonica.

16. A method for sequencing DNA, comprising amplifying DNA by the PCR reaction of claim 11.

17. A method for preparing labeled DNA fragments for hybridization assays comprising amplifying DNA by the PCR reaction of claim 11.

18. The method of claim 1, wherein the plurality of fluctuation cycles between the first extension temperature and the second higher extension temperature includes 20-30 fluctuation cycles in each extension step.

19. The method of claim 1, wherein the plurality of fluctuation cycles between the first extension temperature and the second higher extension temperature includes hundreds of fluctuation cycles in each extension step.

20. The method of claim 1, wherein the one or multiple enzymes include a thermostable DNA polymerase.

21. The method of claim 1, wherein the first lower extension temperature is in the range of 76-78° C.

22. A method for sequencing DNA comprising conducting the primer extension reaction of claim 1.

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: Homo sapiens

<400> SEQUENCE: 1
ccccgccccg cg                                            12